United States Patent
Shalupkin et al.

(10) Patent No.: US 9,440,209 B2
(45) Date of Patent: Sep. 13, 2016

(54) REACTIVE RECTIFICATION COLUMN FOR PERFORMING CHEMICAL REACTIONS

(75) Inventors: Dmitry Nikolaevich Shalupkin, St. Petersburg (RU); Mikhail Al'bertovich Ratasep, St. Petersburg (RU); Oleg Igorevich Parputs, Kirishi (RU); Oleg Valerievich Giyazov, Kirishi (RU)

(73) Assignee: LIMITED COMPANY "REACTIVE RECTIFICATION TECHNOLOGY", St. Petersburg (RU)

( * ) Notice: Subject to any disclaimer, the term of this patent is extended or adjusted under 35 U.S.C. 154(b) by 25 days.

(21) Appl. No.: 14/378,202

(22) PCT Filed: Feb. 13, 2012

(86) PCT No.: PCT/RU2012/000099
§ 371 (c)(1),
(2), (4) Date: Nov. 5, 2014

(87) PCT Pub. No.: WO2013/122496
PCT Pub. Date: Aug. 22, 2013

(65) Prior Publication Data
US 2015/0086430 A1 Mar. 26, 2015

(51) Int. Cl.
*B01J 8/04* (2006.01)
*B01D 3/00* (2006.01)
*C07C 5/27* (2006.01)
*C10G 45/58* (2006.01)

(52) U.S. Cl.
CPC .............. *B01J 8/0492* (2013.01); *B01D 3/009* (2013.01); *B01J 8/0411* (2013.01); *B01J 8/0453* (2013.01); *B01J 8/0465* (2013.01); *C07C 5/277* (2013.01); *C10G 45/58* (2013.01); *B01J 2208/00823* (2013.01); *B01J 2208/00893* (2013.01); *B01J 2208/027* (2013.01)

(58) Field of Classification Search
CPC .... B01J 8/0453; B01J 8/0492; B01J 8/0465; B01J 2208/00893; B01J 2208/0411; B01D 3/009
See application file for complete search history.

(56) References Cited

U.S. PATENT DOCUMENTS

| | | | |
|---|---|---|---|
| 4,842,844 A | 6/1989 | Harris et al. | |
| 5,368,691 A | 11/1994 | Asselineau et al. | |
| 5,493,059 A | 2/1996 | Sanfilippo et al. | |
| 5,776,320 A * | 7/1998 | Marion | B01D 3/009 203/29 |
| 6,045,762 A | 4/2000 | Chuang et al. | |
| 6,048,450 A | 4/2000 | Mikitenko et al. | |
| 2007/0095646 A1 | 5/2007 | Wu et al. | |
| 2012/0184790 A1* | 7/2012 | Giyazov | C10G 45/00 585/269 |

OTHER PUBLICATIONS

International Search Report PCT/RU2012/000099 Dated October 19, 2012.

* cited by examiner

*Primary Examiner* — Lessanework Seifu
(74) *Attorney, Agent, or Firm* — BCF LLP (57) ABSTRACT

A device for performing chemical reactions, in which one starting substance is in the liquid phase and one product is in the gaseous phase, is proposed, comprising a reaction zone which includes two catalytic sections, each section having a feed channel and an overflow well which simultaneously acts as the feed channel for the next section, such that liquid from each section passes into the overflow well of this section and via it enters the lower part of the next section, the device being designed to permit removal of the gaseous products of each section, bypassing the remaining sections.

20 Claims, 10 Drawing Sheets

REACTIVE RECTIFICATION COLUMN FOR PERFORMING CHEMICAL REACTIONS

FIELD OF THE INVENTION

The present invention relates to the field of chemical technology, and in particular to reactors for performing catalytic reactions and reactive-rectification columns.

PRIOR ART

Chemical reactors are apparatuses for performing chemical reactions. Chemical reactions may be performed over a catalyst, in particular over a fixed bed of catalyst. In a number of chemical reactions at least one starting substance is in the liquid phase, and at least one product is in the gaseous phase. Examples of such reactions include the isomerization of paraffins and the hydroisomerization of benzene.

The main problem with most reactions is low selectivity in respect of the target product or a low degree of conversion of the starting substances. Certain reactions require the use of several catalysts and are usually performed using separate devices for each reaction, in which case the overall size of the system and the power consumption are substantial.

A need thus exists for the creation of improved devices for the performance of chemical reactions.

SUBSTANCE OF THE INVENTION

The object of the present invention was to create a device for performing catalytic chemical reactions which would make it possible to achieve the maximum conversion of starting substance and to improve the yield of the target product. The object was to create a device which could preferably be readily modified to suit a wide range of processes, particularly oil-refining processes.

Said object has been achieved in that a device for performing chemical reactions over a fixed bed of catalyst, in which at least one starting substance is in the liquid phase and at least one product is in the gaseous phase, is proposed, comprising a reaction zone which includes at least two catalytic sections situated one under the other or concentrically, each section having a feed channel and an overflow well which simultaneously acts as the feed channel for the next section in the liquid flow direction, such that liquid from each section passes into the overflow well of this section and via it enters the lower part of the next section, the overflow well of the last section in the liquid flow direction being open to permit free outflow of the liquid phase, while a distributor is situated above the feed well of the first section in the liquid flow direction to feed liquid phase into the first section in the liquid flow direction, the device being designed to permit the removal of the gaseous products of each section, bypassing the remaining sections.

It is desirable that at least one overflow well/feed channel forms at least part of the outer rim of the reaction zone.

It is desirable that a feed channel is formed such that the liquid present therein forms a hydraulic seal so that the gaseous phase present in the section cannot enter the feed channel.

In a number of embodiments of the invention the bottom of a section is made blind.

At least one reaction section may have a distribution chamber at the bottom thereof under the catalyst bed and may be designed to permit the delivery of gas through this distribution chamber.

It is desirable that said distribution chamber should contain a device for mixing the liquid phase, which passes from the feed channel into said distribution chamber, with the gaseous phase.

In one of the embodiments of the invention, the proposed device is a reactive-rectification column.

In one of the embodiments of the invention, the proposed device is a reactor.

The device described may in itself be a unit of a reactor or of a reactive-rectification column.

In certain embodiments of the invention, the sections contain different catalysts.

Also proposed is a reactive-rectification column comprising at least one reaction zone, wherein said zone includes at least two catalytic sections situated one under the other or concentrically, where each section has a feed channel and an overflow well which simultaneously acts as the feed channel for the next section, such that liquid from each section passes into the overflow well of this section and via it enters the lower part of the next section, the overflow well of the last section in the liquid flow direction being open to permit free outflow of the liquid phase, while a distributor is situated above the feed well of the first section in the liquid flow direction to feed liquid phase into the first section in the liquid flow direction, the zone being designed to permit the removal of the gaseous products of each section, bypassing the remaining sections.

In one of the embodiments, the sections are disposed one under another.

In preferred embodiments, the sections are formed with the overflow well in the center or around the periphery, and sections with the overflow well in the center or around the periphery alternate.

In preferred embodiments, all the peripheral overflow wells form part of the outer rim of the reaction zone.

In preferred embodiments, the gaseous products of each section are withdrawn through a gas offtake channel (channels), bypassing the remaining sections.

A column according to the invention may comprise at least 2 reaction zones. In this case, said zones may be separated by a mass-transfer device.

In certain embodiments, the zones contain different catalysts, while the sections of each zone contain one and the same catalyst.

A column according to the invention may comprise at least 3 reaction zones, at least two of which are separated by a mass-transfer device.

In one of the embodiments, a column according to the invention comprises 3 reaction zones, wherein one zone, designed for the hydroisomerization of benzene, comprises at least 2 sections, while the other two zones, designed for the isomerization of hexane and pentane, each comprise at least 3, preferably 4 or 5, and more preferably 6, sections.

In yet another embodiment, the sections are disposed concentrically. In this case it is desirable that the column contain at least 2 reaction zones. It is desirable that in such a column the sections form a cellular structure with cavities such that the cavities of the reaction zones are disposed one under another and form a channel for the passage of gaseous phase. In certain embodiments, the empty cells of sections may be formed with fins, so that the channel for the passage of gaseous phase is finned. In a number of embodiments, the empty cells may contain mass-transfer devices.

The inventors have found that it is possible to improve target product yield/target product selectivity with the aid of such an arrangement of the reaction zone.

Unexpectedly, it has also been found that the use of a reaction zone according to the invention makes it possible to reduce heat losses and to reduce the amount of catalyst required.

BRIEF DESCRIPTION OF THE DRAWINGS

FIG. 1. Diagram of a reaction zone in which the sections are disposed one under another. FIG. 1A shows a general view of the zone, while

FIG. 7. One zone of a column with several zones of concentric sections (three-dimensional illustration). 7A—general view, 7B—view in cross-section.

DETAILED DESCRIPTION OF THE INVENTION

The reaction zone arrangement now described may be utilized in reaction apparatuses for the performance of catalytic reactions over a fixed bed of catalyst with gaseous reaction products, and also in apparatuses for reactive rectification.

A catalytic (reaction) section according to the invention is a tray filled with catalyst.

A differing residence time for the reaction mixture in each catalyst bed, which is directly proportional to the volume of catalyst and inversely proportional to the velocity of the raw material stream, can be achieved by selecting the appropriate cubic capacity for the trays.

The catalyst can be retained using a retaining mesh or other suitable device.

Examples of catalysts include catalysts which comprise metals of group VIII of the periodic system of chemical elements, applied to supports such as active aluminum oxide, beta-zeolite, pentasils (type ZSM-5), and mordenite. Said supports may be modified with halogens, such as F and/or Cl, and with other elements. Solid and/or supported heteropolyacids may be used as catalysts. Said catalysts may be promoted with Mn, Fe, the halogens Cl and/or F, and other elements.

Figure 1A:
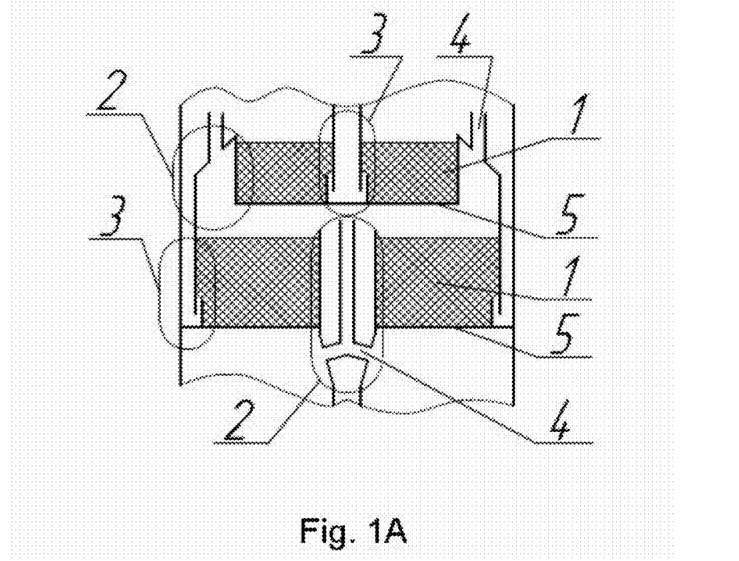
Figure 1B:
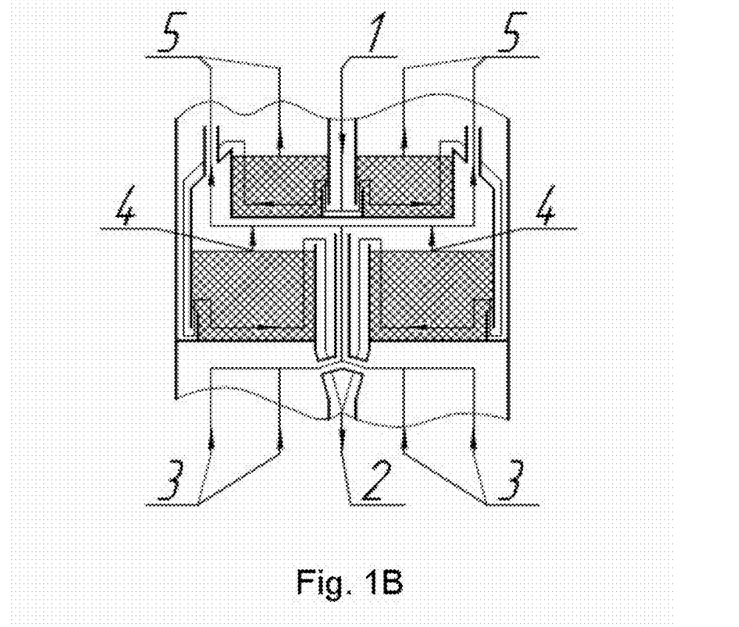
FIG. 1B shows the flow of streams in such a zone.
Figure 5A:
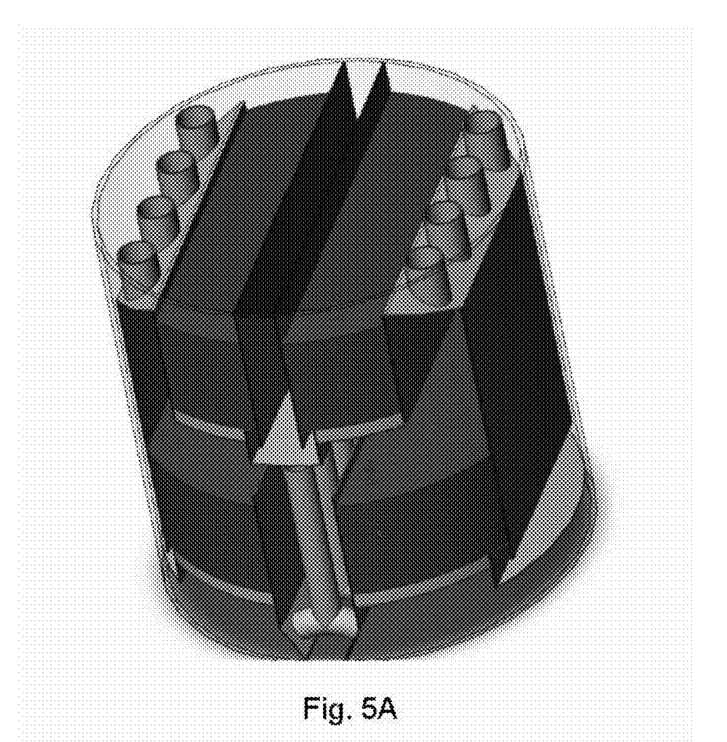
FIG. 5. Three-dimensional illustration of a reaction zone with sections disposed one under another.
Figure 5B:
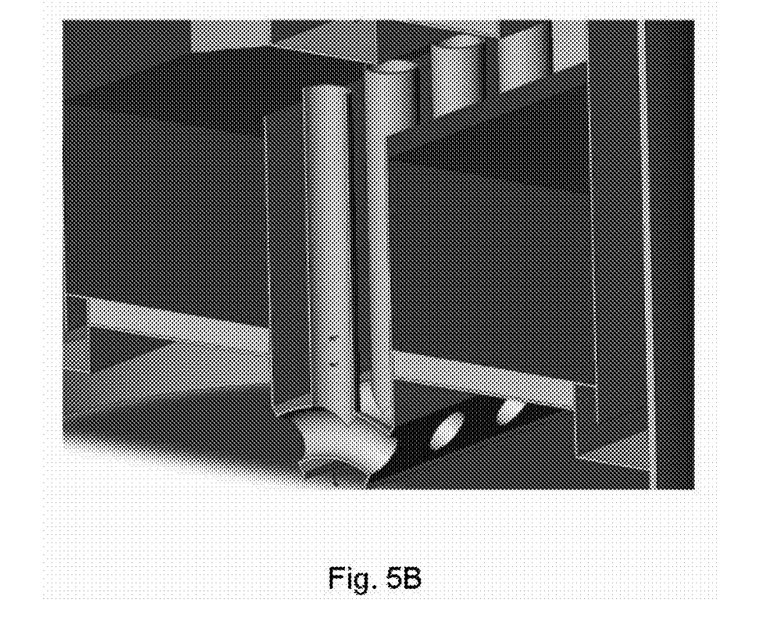

The arrangement of sections one under another is illustrated schematically in FIG. 1. In FIG. 1A, catalyst 1 is disposed in tray 5, and overflow well 2 of the upper section is formed integrally with feed channel 3 of the underlying section, while gas offtake channels 4 pass within overflow wells 2. FIG. 1B shows a diagram of the flow of streams: liquid phase 1 enters the feed channel of the upper section, and passing through the hydraulic seal the liquid phase enters the lower part of the upper section, passes through the catalyst bed, in which a reaction takes place, and via the overflow well flows to the underlying section; there, it passes via the hydraulic seal into the lower part of this section, passes through the catalyst bed, in which a reaction takes place, and via the overflow well flows to the underlying section, or, if this is the final section, flows as free stream 2 to underlying devices. Gaseous phase 3 (when present) passes into the gas offtake channels, and gaseous reaction products 4, which are removed from the uppermost section as stream 5, pass into these same channels. FIG. 5 shows a three-dimensional illustration of such a zone.

Figure 2:
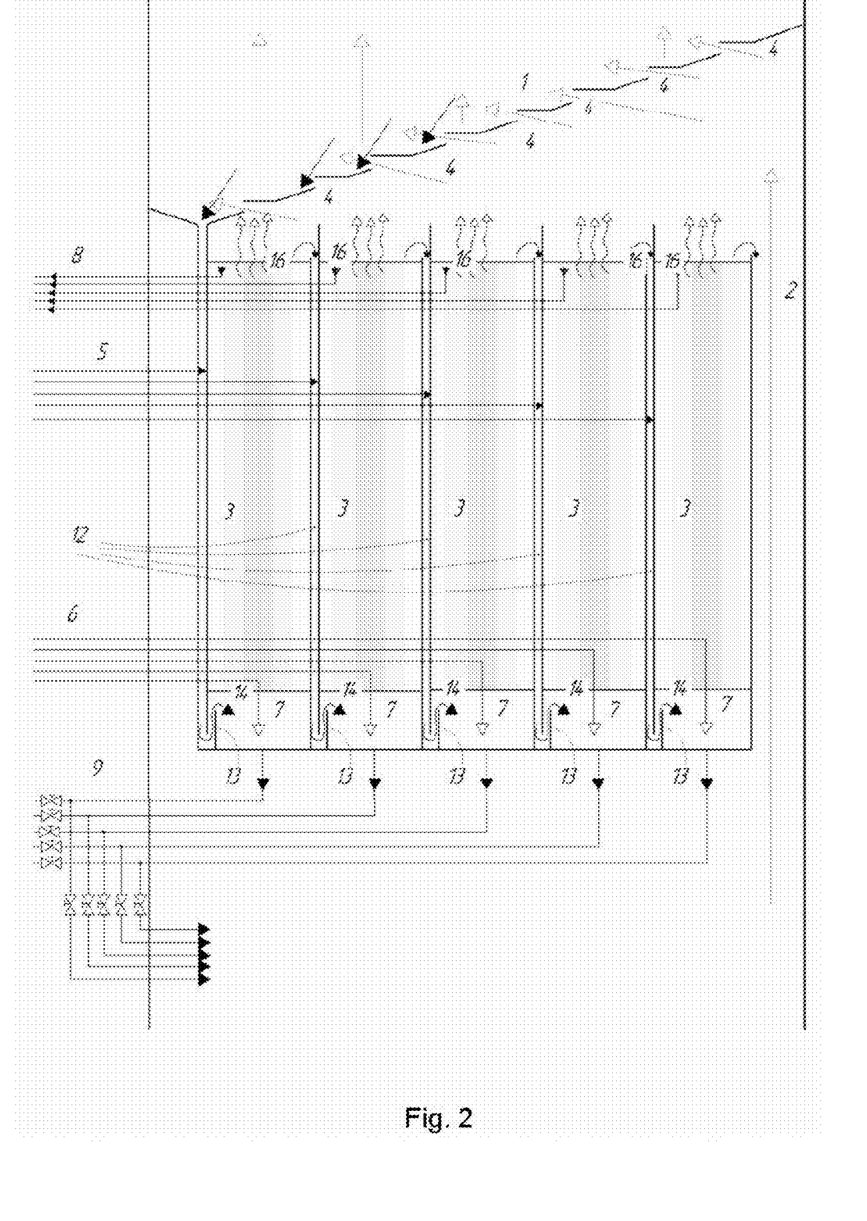
FIG. 2. Diagram of a reaction zone in which the sections are disposed concentrically.

FIG. 2 shows the arrangement of a zone in which the sections are disposed concentrically, i.e. the sections change with increase/decrease in distance from the center of the device.

Liquid collector 1 collects liquid products over the entire cross-section of the apparatus and directs them into feed channel 12 of the first section.

Additional components may be introduced using devices for individual delivery of liquid components 5 into the reaction mixture (via the feed channel).

The reaction mixture then passes into pre-mixing chamber 7, which is separated from the overflow well by hydraulic seal 13, and gas is introduced through a device for individual delivery of gaseous components 6 downwardly into the mixing chamber, as a result of which the reaction mixture is intensively agitated and saturated with the gas, then the well-agitated gas-liquid mixture passes from the pre-mixing chamber through supporting grid 14 into reaction section 3.

The catalyst fill is tightly retained at the top by mesh 16, which prevents entrainment and wear of the catalyst.

At the exit from the reaction section, the gaseous products flow upwards, while the liquid products overflow into overflow well/feed channel 12 of the next reaction section.

The products of each reaction section can be removed with the aid of external offtake devices 8.

With the aid of valves situated outside the apparatus, drainage devices 9 allow reaction sections to be drained and liquid to be drained downwardly within the apparatus or externally, without dismantling the apparatus.

The reaction sections are connected by overflow wells 12, and the sequence of reaction sections through which the liquid products will flow can be changed by opening and closing said wells.

With such an arrangement of the zone, the stream of components is parallelized, which increases the reliability of performance of the reaction: on failure of one reaction section, the remaining sections continue to operate.

Figure 6:
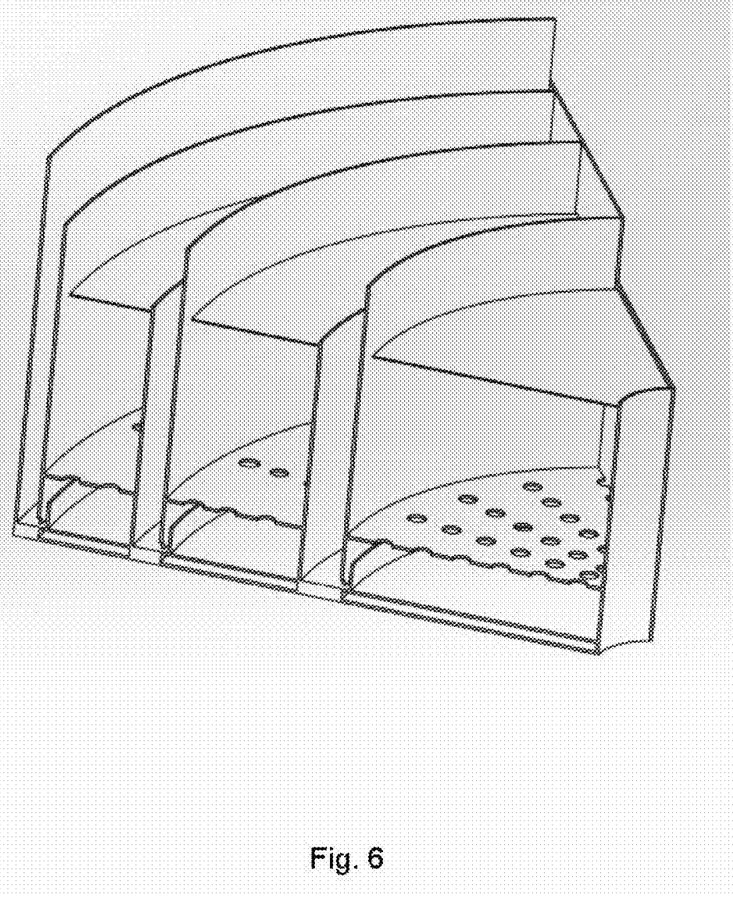
FIG. 6. Three-dimensional illustration of a reaction zone with concentric sections.

A three-dimensional illustration of one of the embodiments of the zone is shown in FIG. 6.

Positioning the reaction devices at the same level curtails the overall height of the apparatus, which reduces power consumption (pumps, heat of evaporation), the volume and cost of structures and in certain loading conditions the total metal consumption: the increase in volume is linearly dependent on height and quadratically dependent on diameter, while the materials consumption increases linearly.

If a single catalyst is employed in the zone, the reaction proceeds in several reaction sections operating in parallel.

If different catalysts are used in the zone, the sequence of flow through these is determined by the sequence in which the overflow wells of the reaction sections are connected. Various schemes for the flow of liquid components can be arranged using the system of overflows, i.e. the catalysts of the system can operate in different sequences.

In certain embodiments, all the reaction zones have individual delivery and offtake of components, while remaining interconnected. The individual delivery of gaseous components makes it possible to adjust the thermodynamics and hydrodynamics of each catalytic system, although there may be a common gas feed for all sections. The individual delivery of liquid components makes it possible to optimize the compositions of the reaction mixtures and to extend the range of chemical reactions being performed.

In principle, reducing the residence time of the liquid phase over a catalyst can increase the yield of the target product by reducing the conversion thereof into subsequent (undesired) products, however the degree of conversion of the initial product is simultaneously reduced. The proposed device makes it possible to reduce the residence time of the liquid phase over a catalyst, but also to reduce the residence time over a catalyst of a gaseous target product, which is taken off from each section. It has thus been possible to increase the target product yield/target product selectivity.

Unexpectedly, it has also been found that the use of a reaction zone according to the invention makes it possible to reduce heat losses and to reduce the amount of catalyst required.

The sectional disposition of the catalyst makes it possible to utilize efficiently the heat liberated in the course of the reaction in the catalyst bed. More specifically, this heat is utilized to heat the reaction mixture, the reaction products and the environment of the apparatus. The effect is achieved firstly by a reduction in the surfaces from which heat is lost to the ambient medium, since the trays which contain the catalyst fill are partially or wholly separated from the wall of the apparatus by a layer of reaction mixture, reaction products or other working medium contained in the overflow wells or feed channels. Secondly, when different reactions are performed in the sections, the sections can be arranged such that the heat liberated in the course of the reaction in the catalyst bed in one section will be utilized directly in an adjacent section. This effect is demonstrated in Example 1.

The device reduces competition of finished products with unreacted components over a catalyst, thus the catalyst is utilized rationally and it is possible to reduce the volume of the catalyst fill compared with the case of an undivided fill.

As a result of the timely removal of reaction products from the reaction zone and, as a consequence, the reduction in competition between the unreacted reaction mixture and the reaction products, it was found possible to reduce the volume of catalyst needed to perform a particular reaction. This effect is demonstrated in Example 2.

Furthermore, such a device makes it possible to carry out reactions with multi-component initial mixtures over various catalysts placed in a single reaction zone. In this case, the reaction products are removed in stages from the reaction sections, which makes it possible to avoid the undesirable contact thereof with the catalysts of other sections, while the liquid phase remains in reaction.

The proposed design also makes it possible to modify the device for a wide range of processes, including oil-refining, and allows catalyst to be loaded and unloaded through a hatch in the wall, i.e. it is technologically advantageous. The design of the reaction zone, implemented in an industrial apparatus, allows loading and unloading in each reaction section via a fitting in the wall of the apparatus, which significantly reduces the time required for preparative operations as compared to analogous devices. The proposed device is distinguished by the simplicity of catalyst loading and unloading.

Figure 4:
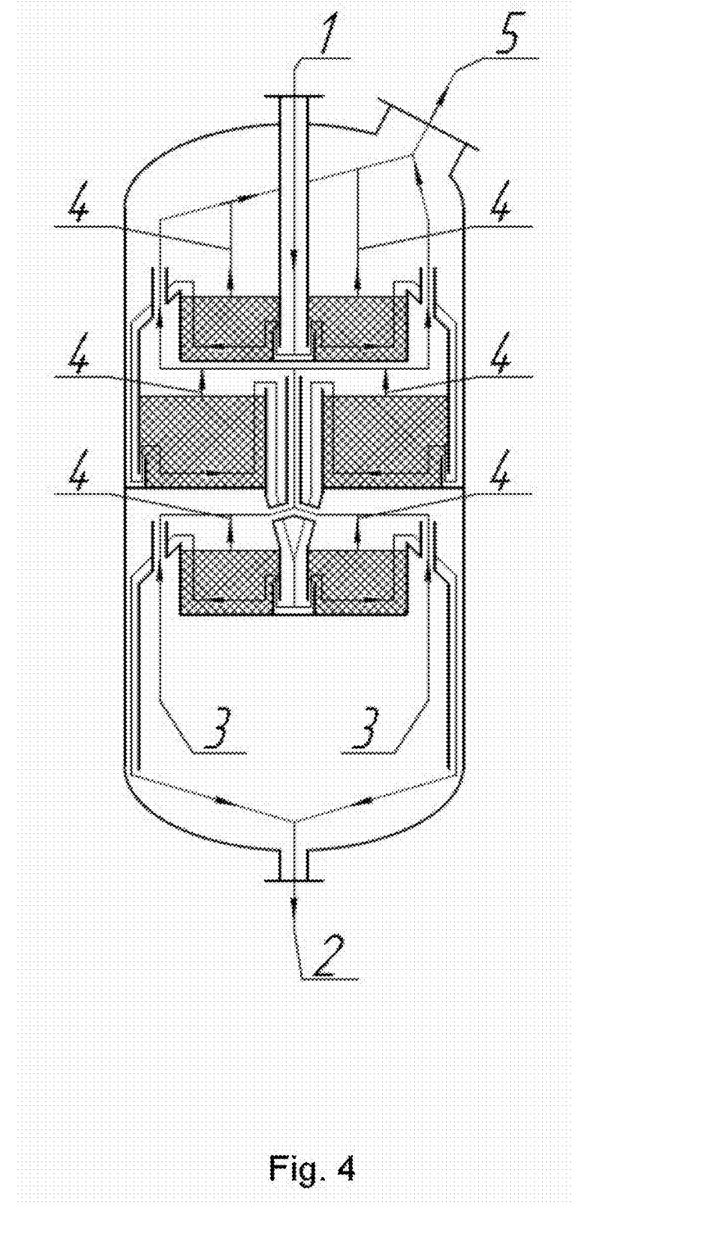
FIG. 4. Diagram of a reactor with a reaction zone according to the invention.

The proposed arrangement of the reaction zone may be applied to reactors. In this case, the reaction mixture is fed into the apparatus from the top and passes into the upper reaction section. It then passes stagewise through all the sections and is discharged from the lower part of the apparatus. A fitting may be provided in the upper part of the apparatus for the offtake of gaseous reaction products. FIG. 4 shows a diagram of the reactor and also of the flows therein: liquid phase 1 passes into the feed channel of the upper section, the liquid phase enters the lower part of the upper section via the hydraulic seal, passes through the catalyst bed, in which a reaction proceeds, and overflows into the underlying section via the overflow well; there it enters the lower part of this section via the hydraulic seal, passes through the catalyst bed, in which a reaction proceeds, and overflows via the overflow well into the underlying section, while from the last section the liquid phase flows as free stream 2 to devices disposed below. Gaseous phase 3 (when present) passes into the gas offtake channels, and gaseous reaction products 4, which are taken off from the uppermost section as stream 5, pass into these same channels.

Figure 9:
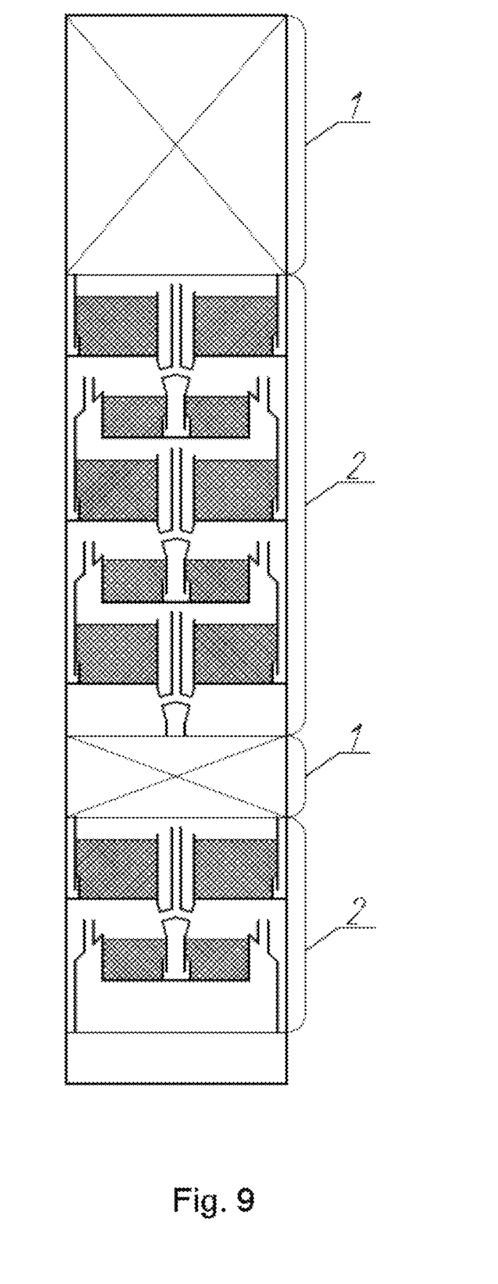
FIG. 9. Diagram of a reactive-rectification column with a reaction zone according to the invention.

The proposed arrangement of the reaction zone can be employed in apparatuses for reactive rectification. The vapor/gas stream from a still or mass-transfer zone enters from below and flows through the gas-offtake channels. A liquid stream enters the reaction zone from the top, in particular from a column head or from a mass-transfer device, and is fed into the feed channel of the upper reaction section. It then passes stagewise through each section and is discharged into the still of the apparatus or into an underlying mass-transfer zone, and then into an underlying reaction zone or still. FIG. 9 shows a diagram of a column.

Figure 7A:
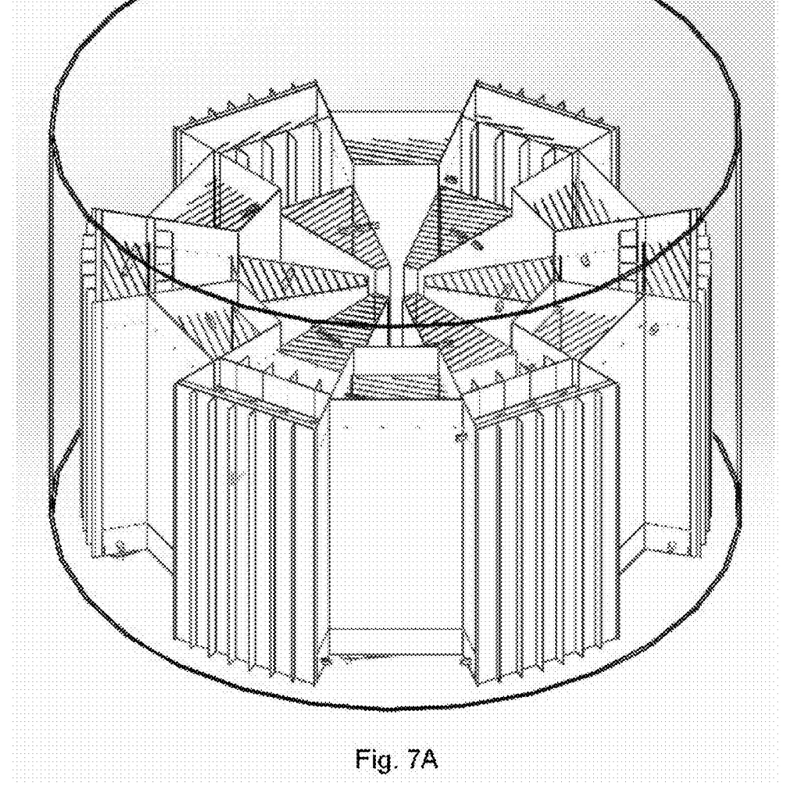
Figure 7B:
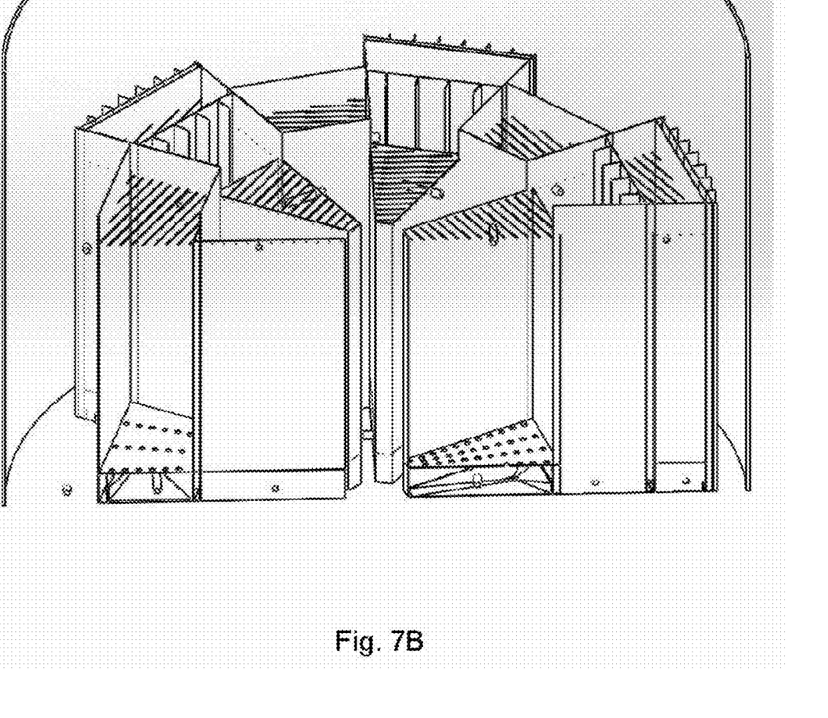
Figure 8A:
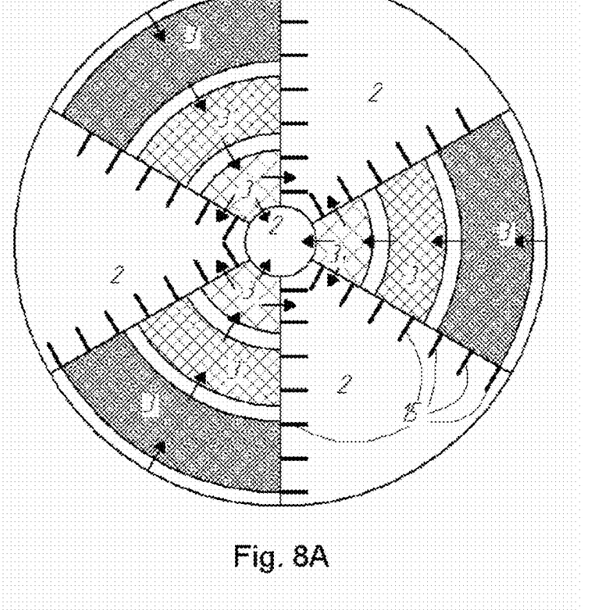
FIG. 8. One zone of a column with several zones of concentric sections (cross-section, variants).
Figure 8B:
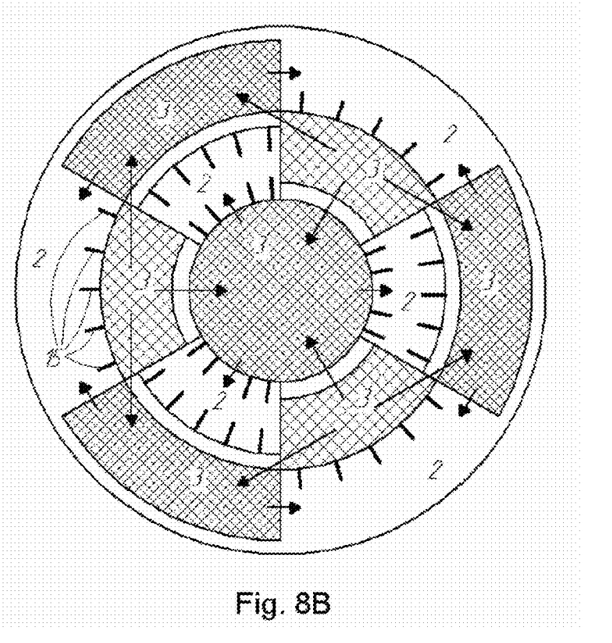

If a column is formed with several zones of concentric sections, the sections may be made cellular, as shown in FIGS. 7 and 8.

As shown in FIG. 7, the reaction cells of sections are uniformly distributed over the cross-section of the apparatus and alternate with transport channels formed by their outer walls, preferably in a staggered arrangement where each reaction cell of one section is connected to two cells of another section.

In this case, the gas offtake (transport) channels are formed by the empty cells of several zones and provide for the transport of gaseous and liquid components. The channels may be made with finning 15 (FIG. 8A) in order to intensify heat and mass transfer. The transport channels allow rising vapor to pass through, bypassing the reaction device, without significant hydraulic losses, allow liquid products to be withdrawn downwardly, and allow mass transfer to be performed between the rising vapor and the falling liquid; other devices can readily be placed and operated in the transport channels. Additional mass-transfer devices, such as packing, may be situated in the transport channels.

In such embodiments, it is desirable to position specific catalysts with allowance for thermal effects; for example it is desirable to position catalytic sections with an exothermal effect in locations which have the greatest wall area in common with the transport channels.

Alternating the cells of the reaction sections with the transport channels makes it possible to reduce the hydraulic resistance of the entire device and to equalize it over the cross-section of the apparatus.

Mass-transfer devices which carry out continuous fractionation may, as is well known to any average specialist, include rectifying plates, unstructured mass-transfer packing, or structured mass-transfer packing.

Figure 3:
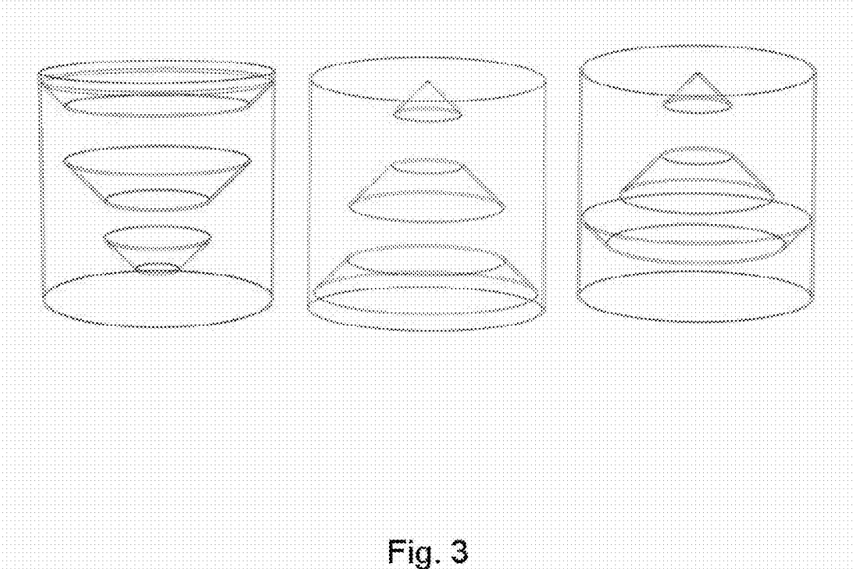
FIG. 3. Variants of a device for collecting liquid components for introduction of liquid phase into the first section.

The device for collecting liquid components ensures that the liquid products are introduced into the required area of the device, depending on where the liquid components are first to be introduced. Examples of arrangements of such devices are shown in FIG. 3. The implementation of a device for collecting liquid components shown in FIG. 2 consists of a series of sequentially connected deflector elements 4, which collect liquid components and form a system of channels for the passage of gaseous components, the device having low hydraulic resistance due to the large area of the channels.

The hydraulic seal in the feed channels is arranged such that the wall of the channel/well descending from the top extends to below the height of the hydraulic seal wall which extends from the bottom.

The gaseous products of each section may be taken off, bypassing the remaining sections, through gas offtake channels, which may be led through the feed channels (overflow wells) in order to save space. In this case, the vapor/gas stream does not contact either the catalytic system or the liquid stream of reaction mixture. Thanks to this, the reaction zone operates in stable hydrodynamic conditions (with no flooding or slumping) within wide output limits in respect of the liquid and vapor/gas streams, and also restricts pressure differentials in the apparatus.

EXAMPLE 1

Hydroisomerization of benzene in a laboratory unit (a flow reactor).

In a test, the appropriate catalyst was loaded into a device in which the reaction zone was not divided into sections, and a device according to the invention, containing a zone of two sections. The volume of catalyst placed in the apparatus was 30 cm$^3$. The initial component (benzene) was fed at a rate of 90 ml/h. The pressure in the apparatus was 15 kg/cm$^2$ gauge. A temperature of 200° C. was maintained in the reactor with the aid of a cooling water jacket. Part of the heat generated in the course of the reaction was removed in heating the reaction mixture, the reaction products and the operating environment of the apparatus, while another part was dissipated in heating the walls of the apparatus and losses to the ambient environment. The thermal flux removed from the walls of the reactor was calculated from the final temperature of the cooling water (with a constant initial temperature and constant flow rate). For the reaction zone of the comparison device, the thermal flux through the walls of the reactor was 21.7 W. For the reaction zone according to the invention, the thermal flux through the walls of the apparatus was 13.3 W.

A reduction in thermal losses was thus achieved.

EXAMPLE 2

Isomerization of pentane in a laboratory unit (a flow reactor).

When using a device in which the reaction zone was not divided into sections, and feeding the initial component (pentane) at a rate of 60 ml/h, a catalyst volume of 30 cm$^3$ had to be loaded in order to achieve a degree of conversion of 68%. When the experiment was performed with a reaction zone according to the invention, consisting of six reaction sections, 26 cm$^3$ of catalyst had to be loaded in order to secure the same conversion value, other conditions being equal.

EXAMPLE 3

Multistage reactions with stagewise selectivity. Isomerization of hexane.

In the first stage, methylpentane is formed on contact between hexane and the appropriate catalyst. The methylpentane is then converted into dimethylbutanes. Further contact between the dimethylbutanes and the same catalyst leads to cracking with the formation of lighter hydrocarbons. The target components in oil refining are the dimethylbutanes. Performing said reaction in a reaction zone according to the invention makes it possible to achieve the maximum yield of dimethylbutanes by selecting the dimensions of the reaction sections and the number thereof, other conditions being equal with devices known from the prior art.

The invention claimed is:

1. A device for performing chemical reactions over a fixed bed of catalyst, in which at least one starting substance is in the liquid phase and at least one product is in the gaseous phase, comprising a reaction zone which includes at least two catalytic sections situated one under the other, each section having a feed channel and an overflow well which simultaneously acts as the feed channel for the next section in the liquid flow direction, such that liquid from each section passes into the overflow well of this section and via it enters the lower part of the next section, the overflow well of the last section in the liquid flow direction being open to permit free outflow of the liquid phase, while a distributor is situated above the feed well of the first section in the liquid flow direction to feed liquid phase into the first section in the liquid flow direction, the device being designed to permit the removal of the gaseous products of each section, bypassing the remaining sections.

2. The device as claimed in claim 1, wherein at least one overflow well/feed channel forms at least part of the outer rim of the reaction zone.

3. The device as claimed in claim 1, wherein a feed channel of at least one of the at least two catalytic sections is formed such that the liquid present in the feed channel forms a hydraulic seal so that the gaseous phase present in the at least one of the at least two catalytic sections cannot enter the feed channel.

4. The device as claimed in claim 1, wherein the bottom of at least one of the at least two catalytic sections is made blind.

5. The device as claimed in claim 1, wherein at least one reaction section has a distribution chamber at the bottom thereof under the catalyst bed and is designed to permit the delivery of gas through this distribution chamber.

6. The device as claimed in claim 5, wherein said distribution chamber contains a device for mixing the liquid phase, which passes from the feed channel into said distribution chamber, with the gaseous phase.

7. The device as claimed in claim 1, which comprises a reactive-rectification column.

8. The device as claimed in claim 1, which comprises a reactor.

9. The device as claimed in claim 1, which comprises a unit of a reactor or of a reactive-rectification column.

10. The device as claimed in claim 1, wherein the sections contain different catalysts.

11. A reactive-rectification column comprising at least one reaction zone, wherein said zone includes at least two catalytic sections situated one under the other, each section having a feed channel and an overflow well which simultaneously acts as the feed channel for the next section, such that liquid from each section passes into the overflow well of this section and via it enters the lower part of the next section, the overflow well of the last section in the liquid flow direction being open to permit free outflow of the liquid phase, while a distributor is situated above the feed well of the first section in the liquid flow direction to feed liquid phase into the first section in the liquid flow direction, the zone being designed to permit the removal of the gaseous products of each section, bypassing the remaining sections.

12. The column as claimed in claim 11, wherein the sections are formed with the overflow well in the center or around the periphery, and sections with the overflow well in the center or around the periphery alternate.

13. The column as claimed in claim 12, wherein all the peripheral overflow wells form part of the outer rim of the reaction zone.

14. The column as claimed in claim 11, wherein the gaseous products of each section are withdrawn through a gas offtake channel (channels), bypassing the remaining sections.

15. The column as claimed in claim 11, which comprises at least 2 reaction zones.

16. The column as claimed in claim 15, wherein said zones are separated by a mass-transfer device.

17. The column as claimed in claim 15, wherein the zones contain different catalysts, while the sections of each zone contain one and the same catalyst.

18. The column as claimed in claim 15, comprising at least 3 reaction zones, at least two of which are separated by a mass-transfer device.

19. The column as claimed in claim 18, comprising 3 reaction zones, wherein one zone, designed for the hydroisomerization of benzene, comprises at least 2 sections, while the other two zones, designed for the isomerization of hexane and pentane, each comprise at least 3 sections and at most 6 sections.

20. The column as claimed in claim 18, comprising 3 reaction zones, wherein one zone, designed for the hydroisomerization of benzene, comprises at least 2 sections, while the other two zones, designed for the isomerization of hexane and pentane, each comprise 6 sections.

\* \* \* \* \*